(12) United States Patent
Realmuto et al.

(10) Patent No.: US 11,510,841 B2
(45) Date of Patent: Nov. 29, 2022

(54) ROBOTIC FOREARM ORTHOSIS USING SOFT FABRIC-BASED HELICAL ACTUATORS

(71) Applicants: Jonathan Realmuto, Irvine, CA (US); Terence D. Sanger, Irvine, CA (US)

(72) Inventors: Jonathan Realmuto, Irvine, CA (US); Terence D. Sanger, Irvine, CA (US)

( * ) Notice: Subject to any disclaimer, the term of this patent is extended or adjusted under 35 U.S.C. 154(b) by 0 days.

(21) Appl. No.: 17/602,084

(22) PCT Filed: Apr. 9, 2020

(86) PCT No.: PCT/US2020/027540
§ 371 (c)(1),
(2) Date: Oct. 7, 2021

(87) PCT Pub. No.: WO2020/214489
PCT Pub. Date: Oct. 22, 2020

(65) Prior Publication Data
US 2022/0096309 A1   Mar. 31, 2022

Related U.S. Application Data

(60) Provisional application No. 62/833,893, filed on Apr. 15, 2019.

(51) Int. Cl.
*A61H 1/02* (2006.01)
(52) U.S. Cl.
CPC ... *A61H 1/0285* (2013.01); *A61H 2001/0203* (2013.01); *A61H 2201/10* (2013.01);
(Continued)
(58) Field of Classification Search
CPC .......... A61H 1/0285; A61H 2001/0203; A61H 2201/10; A61H 2201/1246;
(Continued)

(56) References Cited

U.S. PATENT DOCUMENTS 4,976,191 A  *  12/1990  Suzumori ............... F01B 19/00
                                                         92/48
9,835,184 B2     12/2017  Bishop-Moser et al.
(Continued)

FOREIGN PATENT DOCUMENTS

WO    2018222930 A1    12/2018

OTHER PUBLICATIONS

Patent Cooperation Treaty (PCT) Notification Concerning Transmittal of International Preliminary Report on Patentability (Chapter 1 of the Patent Cooperation Treaty) regarding PCT/US2020/027540; received from epct-noreply@wipo.int on Oct. 28, 2021; 1 page.

(Continued)

*Primary Examiner* — Justine R Yu
*Assistant Examiner* — Benjamin M. Kusiak
(74) *Attorney, Agent, or Firm* — Cislo & Thomas, LLP

(57) ABSTRACT

A robotic orthosis device for assisting users to rotate their wrist with a pair of fabric-based helical actuators and a sleeve or rigid interfaces configured to attach to a user's forearm. Each of the helical actuators includes a cylinder and a pneumatic bladder configured to inflate the cylinder. Each cylinder includes an anisotropic sheet material and a base sheet material running the length of the cylinder. The anisotropic sheet material comprises elastomeric strands that enable the material to stretch in a direction parallel to the orientation of the elastomeric strands, but different than the longitudinal axis of the cylinder. The base sheet material, which is affixed to the anisotropic sheet material, is strain-limiting along the longitudinal axis. When the bladder is pressurized, the expansion of the bladder causes the cylinder to stretch and twist, thus generating a helical force on the user' wrist relative to the elbow.

18 Claims, 16 Drawing Sheets

(52) U.S. Cl.
CPC ............... *A61H 2201/1246* (2013.01); *A61H 2201/165* (2013.01); *A61H 2201/1635* (2013.01); *A61H 2201/1673* (2013.01); *A61H 2201/5071* (2013.01); *A61H 2230/605* (2013.01)

(58) Field of Classification Search
CPC ...... A61H 2201/1635; A61H 2201/165; A61H 2201/1673; A61H 2201/5071; A61H 2230/605; A61H 1/0274; A61H 1/0277–0281; A61H 1/0288; A61H 1/0237–0266; A61H 2201/0103; A61H 2201/1238; A61H 2201/1409; A61H 3/00; F15B 15/10; F15B 15/103; A61F 2/68; A61F 2/70; A61F 5/013; A61F 2005/0151; A61F 2005/0155; A61F 2005/0159; B25J 9/142; B25J 9/0006; B25J 9/0009; B25J 9/0012; B25J 13/081; B25J 13/088; B25J 15/0023; B25J 15/12; A41D 13/08; A41D 13/088
USPC ............................................................. 601/5
See application file for complete search history.

(56) References Cited

U.S. PATENT DOCUMENTS

| | | | | |
|---|---|---|---|---|
| 10,828,788 | B2* | 11/2020 | Lessing | B25J 9/142 |
| 10,974,382 | B2* | 4/2021 | Lessing | B25J 15/083 |
| 2013/0030277 | A1* | 1/2013 | Fahey | A61H 39/002 |
| | | | | 607/48 |
| 2014/0318118 | A1* | 10/2014 | Mazzeo | F03G 7/06 |
| | | | | 60/527 |
| 2015/0090113 | A1* | 4/2015 | Galloway | B25J 9/142 |
| | | | | 92/48 |
| 2016/0052131 | A1* | 2/2016 | Lessing | B25J 13/08 |
| | | | | 361/679.01 |
| 2016/0107309 | A1* | 4/2016 | Walsh | A61B 5/6831 |
| | | | | 248/550 |
| 2016/0114482 | A1* | 4/2016 | Lessing | B25J 15/083 |
| | | | | 294/196 |
| 2016/0252110 | A1 | 9/2016 | Galloway et al. | |
| 2016/0263751 | A1 | 9/2016 | Galloway | |
| 2017/0231787 | A1* | 8/2017 | Noda | B25J 9/144 |
| | | | | 623/26 |
| 2018/0207814 | A1* | 7/2018 | Lessing | B25J 9/142 |
| 2019/0015233 | A1 | 1/2019 | Galloway et al. | |
| 2019/0374422 | A1 | 12/2019 | Yeow | |

OTHER PUBLICATIONS

Patent Cooperation Treaty (PCT) International Preliminary Report on Patentability (Chapter 1 of the Patent Cooperation Treaty) regarding PCT/US2020/027540; received from epct-noreply@wipo.int on Oct. 28, 2021; 6 pages.

"Hydrogel Electrodes What you should know about Hydrogel Electrodes", Terasigma Enabling Pain Relief; www.terasigma.com; 6 pages.

PCT International Search Report and Written Opinion of PCT Patent Application No. PCT/US2020/027540 dated Jun. 25, 2020; 13 pages.

* cited by examiner

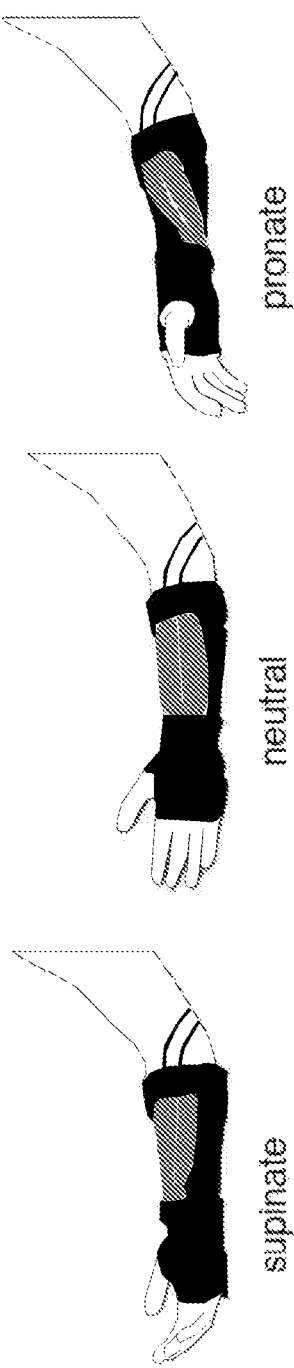
Fig. 3A supinate Fig. 3B neutral Fig. 3C pronate

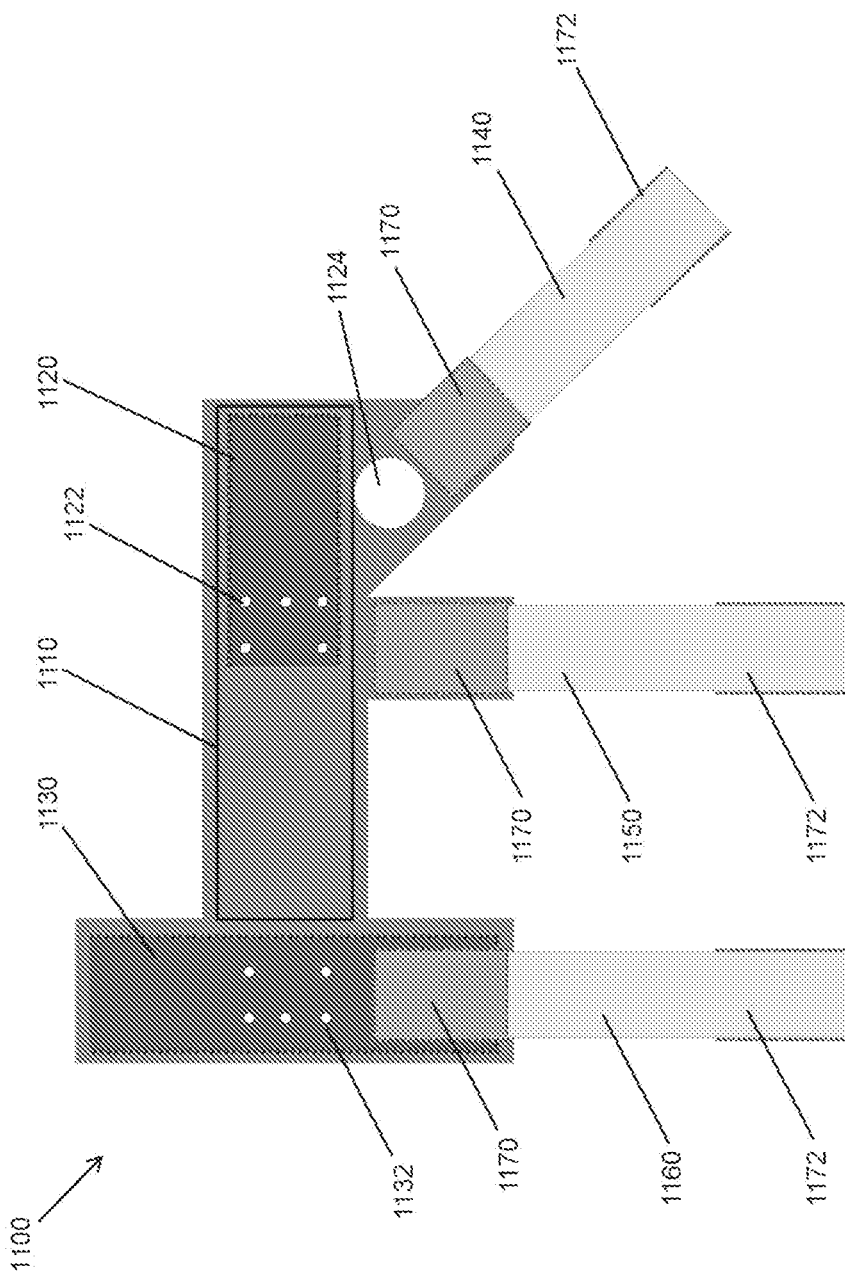

ROBOTIC FOREARM ORTHOSIS USING SOFT FABRIC-BASED HELICAL ACTUATORS

CROSS-REFERENCE TO RELATED APPLICATION(S)

This application claims the benefit of U.S. Provisional Patent Application Ser. No. 62/833,893 filed Apr. 15, 2019, titled "A ROBOTIC FOREARM ORTHOSIS USING SOFT FABRIC-BASED HELICAL ACTUATORS," which provisional patent application in its entirety is hereby incorporated by reference herein for all purposes.

TECHNICAL FIELD

In at least one aspect, the present invention is related to a robotic orthosis, and in particular, to robotic orthosis for assisting in forearm movement.

BACKGROUND ART

For people with movement disorders, such as Parkinson disease (PD), dystonia, tremor, and stroke induced hemiparesis, completing activities of daily living (ADLs) poses a significant challenge. Many essential ADLs, e.g., pouring from a pitcher, operating knobs, self-feeding, and opening a door, require substantial forearm pronation and supination (axial rotation of the wrist). Traditional upper limb robotic orthoses, i.e., rigid exoskeletons, can assist in movement, thus offering increased independence. However, rigid robotic structures are often stationary, have kinematic incompatibilities when the robot and human joints are misaligned, and can add substantial inertia with respect to movement of segments of the human body.

Advances in soft robotics are enabling a new generation of lightweight, compliant and wearable robots. Soft robotic approaches may offer many advantages over rigid exoskeletons including lightweight, compliance, portability, and ease of donning/doffing. Nevertheless, little research has been invested into soft wearable robots that assist in forearm supination/pronation. Accordingly, there is a need for wearable robotics for forearm supination/pronation that are both lightweight, easy to affix, and inexpensive.

SUMMARY OF INVENTION

The present invention solves one or more problems of the prior art by a providing robotic forearm orthosis that integrates an antagonistic pair of soft fabric-based helical actuators. In at least one aspect, the fabric-based actuators produce helical motion, specifically pronation and supination torque, for driving a robotic forearm orthosis. For tasks requiring forearm rotation, an increase in torque assistance effectively decreases the user's effort. On average, the proposed robotic orthosis reduced the effort by 59% and 24%.

In some embodiments, the robotic orthosis device comprises a user mounting system and at least one helical actuator. The user mounting system is configured to attach the at least one actuator to the user's wrist, hand, and/or forearm. The at least one helical actuator includes a cylinder and a bladder. The cylinder is made of portions of fabric including an anisotropic sheet material and base sheet material. The anisotropic sheet material comprises elastomeric strands all of which are oriented in a single direction. The elastomeric strands are oriented in a direction non-parallel to the longitudinal axis of the cylinder. The anisotropic sheet material is flexible in the direction parallel to the longitudinal axis of the cylinder (compared to the base sheet material), but is most flexible in the direction parallel to the elastomeric strands. The base sheet material, which is affixed to the anisotropic sheet material, is substantially inelastic and is strain-limiting in the direction along the longitudinal axis of the cylinder. When the bladder is inflated with air pressure, the bladder expands against the inner walls of the cylinder which, in turn, causes the cylinder to deform and twist in a helical manner, thus inducing a rotational motion in the user's arm and/or wrist.

In the preferred embodiment, the robotic orthosis device comprises both a supination actuator and pronation actuator, which are configured to provide equal but opposite torque. The supination actuator comprises a first anisotropic sheet material and the pronation actuator comprises a second anisotropic sheet material. The first anisotropic sheet material is characterized by a first principle strain axis, and the second anisotropic sheet material is characterized by a second principle strain axis. The angle between the first principle strain axis and the longitudinal axis of the cylinder is between 10 and 80 degrees, while the angle between the second principle strain axis and the longitudinal axis is between −10 and −80 degrees. The supination and pronation actuators are therefore antagonistic.

The two anisotropic sheet materials are, in some embodiments, affixed to a single base sheet material and the base sheet material affixed to the user mounting system. The user mounting system may include a flexible sleeve or rigid interfaces with hydrogel pads and hook and loop straps to adhere the interfaces to the user's arm. The hydrogel pads may include embedded sensors configured to sense muscle activation and/or interaction forces (i.e., force the user is exerting on the orthosis) of the user and drive the supination or pronation actuator based, in part, on the muscle activation. In some embodiments, the hydrogel pads may also include electrical contacts configured to provide muscle and/or nerve stimulation to the user and sense the user response.

In some embodiments, the invention includes a helical actuator comprising: a fabric-based cylinder having a longitudinal axis, and a bladder configured to inflate and apply pressure against the cylinder. The cylinder comprises an anisotropic sheet material and base sheet material. The anisotropic sheet material comprises elastomeric strands, all the elastomeric strands being oriented in a first direction and the first direction is different than the longitudinal axis of the cylinder. The base sheet material is affixed to the anisotropic sheet material, wherein the base sheet material is strain-limiting along the longitudinal axis. The anisotropic sheet material is therefore more extendible in a direction along the cylinder's longitudinal axis than the base sheet material.

BRIEF DESCRIPTION OF THE DRAWINGS

FIGS. 3A-3C include photos of a robotic forearm orthosis in supination mode, neutral mode, and pronation mode;

FIG. 11A is a robotic wrist orthosis with antagonist fabric-based helical actuators, neoprene sleeve with pockets for support inserts, and elastic straps;

DESCRIPTION OF EMBODIMENTS

Reference will now be made in detail to presently preferred compositions, embodiments and methods of the present invention, which constitute the best modes of practicing the invention presently known to the inventors. The Figures are not necessarily to scale. However, it is to be understood that the disclosed embodiments are merely exemplary of the invention that may be embodied in various and alternative forms. Therefore, specific details disclosed herein are not to be interpreted as limiting, but merely as a representative basis for any aspect of the invention and/or as a representative basis for teaching one skilled in the art to variously employ the present invention.

It is also to be understood that this invention is not limited to the specific embodiments and methods described below, as specific components and/or conditions may, of course, vary. Furthermore, the terminology used herein is used only for the purpose of describing particular embodiments of the present invention and is not intended to be limiting in any way.

It must also be noted that, as used in the specification and the appended claims, the singular form "a," "an," and "the" comprise plural referents unless the context clearly indicates otherwise. For example, reference to a component in the singular is intended to comprise a plurality of components.

The term "comprising" is synonymous with "including," "having," "containing," or "characterized by." These terms are inclusive and open-ended and do not exclude additional, unrecited elements or method steps.

The phrase "consisting of" excludes any element, step, or ingredient not specified in the claim. When this phrase appears in a clause of the body of a claim, rather than immediately following the preamble, it limits only the element set forth in that clause; other elements are not excluded from the claim as a whole.

The phrase "consisting essentially of" limits the scope of a claim to the specified materials or steps, plus those that do not materially affect the basic and novel characteristic(s) of the claimed subject matter.

With respect to the terms "comprising," "consisting of," and "consisting essentially of," where one of these three terms is used herein, the presently disclosed and claimed subject matter can include the use of either of the other two terms.

Figure 1A:
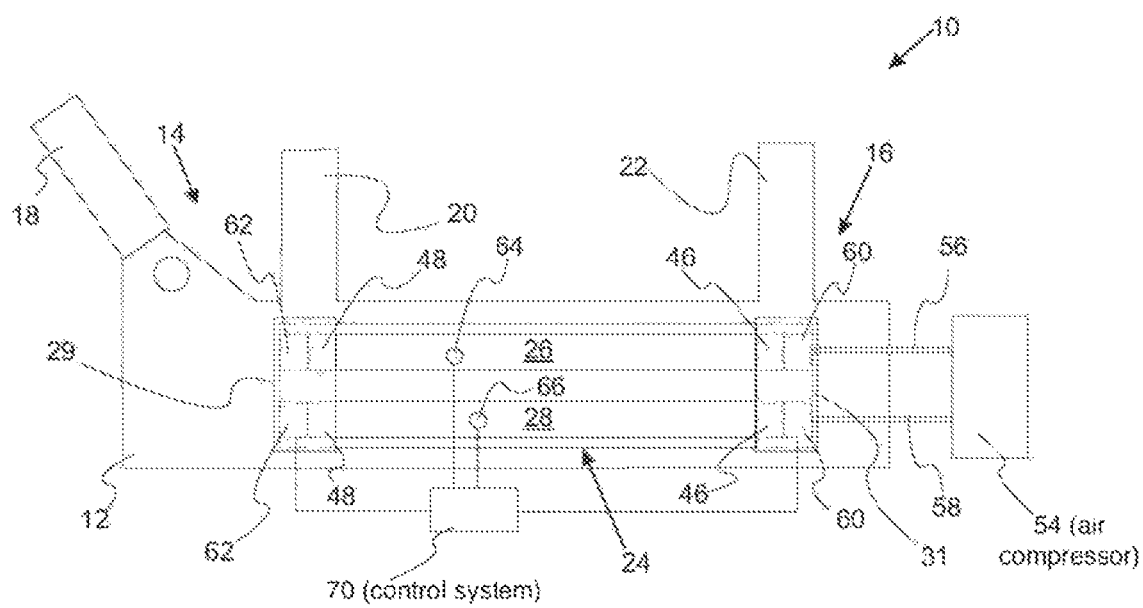
FIG. 1A is a side view of a robotic forearm orthosis.
Figure 1B:
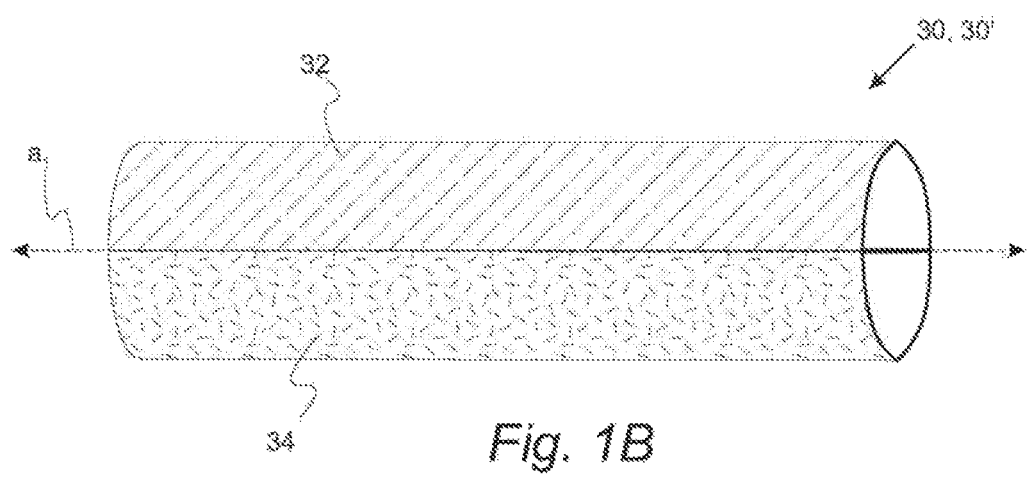
FIGS. 1B-1C are views of a fabric portion of a helical actuator for use in a robotic forearm orthosis.

Illustrated in FIGS. 1A and 1B is a robotic orthosis device 10, in accordance with one embodiment of the present invention. The robotic orthosis device 10 includes a wearable sleeve 12 comprising a first mount 14, second mount 16, and helical actuator system 24. The first mount 14 is configured to detachably attach the wearable sleeve 12 to a user's wrist and/or hand, while the second mount 16 is configured to detachably attach the wearable sleeve to the user's forearm. The first mount 14 includes straps 18, 20 while the second mount 16 includes strap 22. The helical actuation system 24 includes first helical actuator 26 and second helical actuator 28, each of which is mounted on sleeve 12 via brackets 29, 31. The first helical actuator 26 is configured to rotate in a first direction when actuated while the second helical actuator 28 is configured to rotate in a second direction when actuated. In the preferred embodiment, the first direction and second direction are substantially parallel but opposite directions.

In the preferred embodiment, the first helical actuator 26 and second helical actuator 28 are fabric-based helical actuators, each comprising a fabric portion and an inflatable bladder. The fabric portion of an exemplary fabric-based helical actuator is illustrated in FIG. 1B. The fabric portion is configured to form a hollow cylinder 30 (or 30') characterized by a longitudinal axis $a_1$. The hollow cylinder 30 (or 30') consists of an anisotropic sheet material 32 and a base sheet material 34.

The anisotropic sheet material 32 is constructed from a first fabric configured to strain along the longitudinal axis $a_1$ while the base sheet material 34 is constructed from a second fabric that is strain-limiting along the longitudinal axis $a_1$ as compared to the first fabric. That is to say, the second fabric is nearly inelastic or substantially less elastic than the first fabric. In the preferred embodiment, the first fabric is an anisotropic material referred to herein as "knitted elastic fabric". An anisotropic material is a fabric in which the elasticity of the fabric varies depending on the direction in which the strain is induced across the fabric.

In the preferred embodiment, the knitted elastic fabric comprises parallel elastic strands that traverse one direction in the material but not perpendicular to that direction. The orientation of maximum elasticity is referred to herein as the principle strain axis. The knitted elastic fabric is more extendible in a direction coinciding with the parallel elastic strands than the direction perpendicular to the parallel elastic strands. In addition, the anisotropic sheet material 32 is more extendible than the base sheet material 34 with respect to both the longitudinal axis $a_1$ as well as the direction of the parallel elastic strands, i.e., the principle strain axis.

Figure 1C:
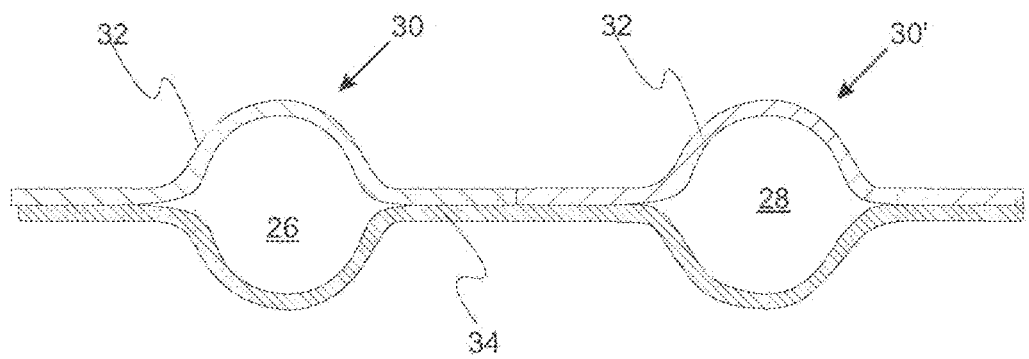

As illustrated in the axial view in FIG. 1C, the hollow cylinders 30, 30' that form the first helical actuator 26 and second helical actuator 28, respectively, are comprised of three portions of fabric. The base sheet material 34 provides a common base for both hollow cylinders 30, 30'. An anisotropic sheet material 32 is then sewn, glued, or otherwise affixed to the base sheet material 34 to form the hollow cylinder 30, and an additional anisotropic sheet material 32 also sewn, glued, or otherwise affixed to the base sheet material 34 to form the other hollow cylinder 30'. The orientation of the anisotropic sheet material 32 that forms the hollow cylinder 30 is different than the orientation of the anisotropic sheet material 32 that forms the hollow cylinder 30'. As described in more detail below, the different orientations produce different and opposing rotational forces.

Figure 1D:
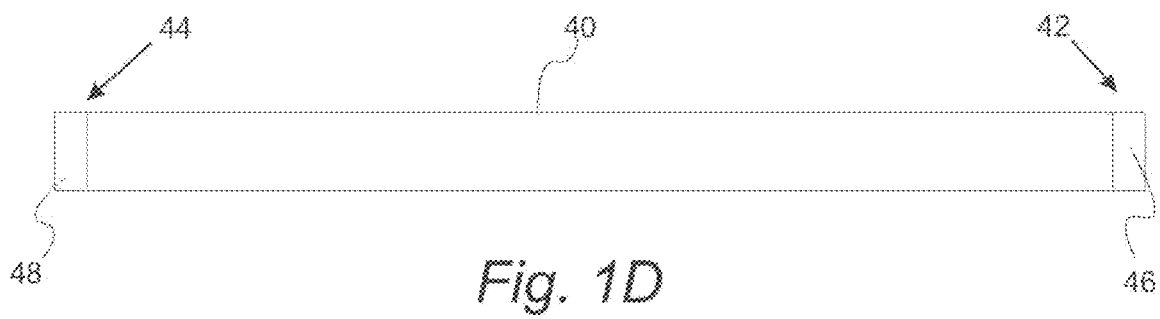
FIGS. 1D-1E are views of an inflatable bladder portion of a helical actuator for use in a robotic forearm orthosis.

As illustrated in FIG. 1D, the first helical actuator 26 and second helical actuator 28 each comprise a pneumatic bladder 40 configured to expand in response to pressurized air or other working fluid. The bladder 40 comprises an inlet end 42 with a first pressure fitting 46 and first solenoid valve configured to receive the pressured air. The bladder 40 further comprises an outlet end 44 with a second pressure fitting 48 and second solenoid valve configured to discharge the pressurized air.

Figure 1E:
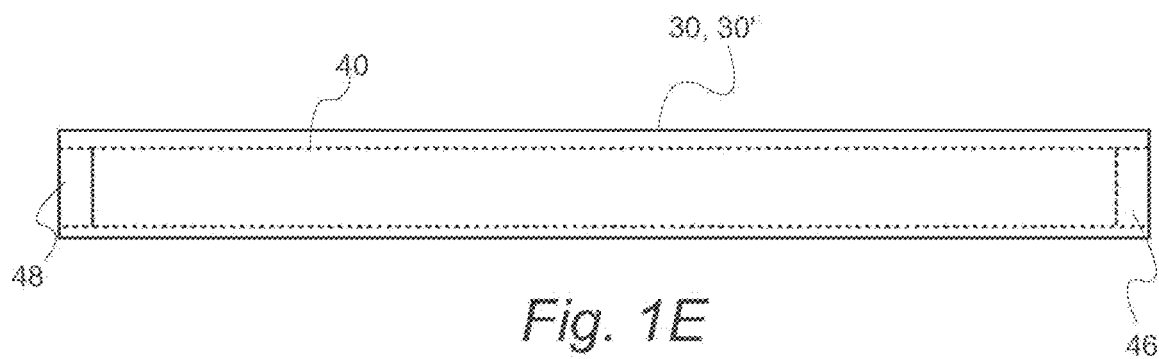

As illustrated in FIG. 1E, a pneumatic bladder 40 is disposed within a hollow cylinder 30 (or 30') where it is configured to apply pressure to the inner walls of the hollow cylinder 30 (or 30'). In particular, pressurized air in the bladder 40 causes the bladder to inflate which, in turn, causes the anisotropic sheet material 32 to stretch in a constrained manner to produce the helical motion of the hollow cylinder. While the working fluid is air in the preferred embodiment, the present invention may also employ other gases or hydraulic fluid to drive actuation. In some embodiments, the robotic orthosis 10 may also include a pressure controller system 70 and air compressor 54 or other a fluid source in fluid communication with the bladder via tubing 56 and 58.

Referring to FIG. 1A again, the first solenoid valve 60 controls the flow of fluid to the bladders 40 through the inlet end while the second solenoid valve 62 controls fluid flow out of the bladder through the outlet end. The robotic orthosis device 10 also includes at least two pressure sensor 64, 66 that measures the air pressure in the bladders 40 of the two actuators. In a refinement, a control system 70 is used to control the first solenoid valve 60 and the second solenoid valve 62 based on signals from the first pressure sensor 64 and the second pressure sensor 66. During operation, the first solenoid valve 60 is opened to allow fluid into one of the bladders to pressurize the bladder and drive the associated actuator. When the desired motion is induced, the appropriate pressure is achieved and the first solenoid value closed to stop the actuation. To return the robotic orthosis device 10 to its unbiased orientation, the second solenoid valve 62 may be opened and the air exhausted from the bladder.

In accordance with the preferred embodiment, the amount of the angular rotation generated by the helical actuators is determined based, in part, on the pressure in the bladder 40 as well as the orientation of the principle strain axis of the anisotropic sheet material of the helical actuator. As set forth in more detail below, a knit angle ϕ denoting the angle between a principle strain axis of the anisotropic sheet material 32 and the longitudinal axis of the hollow cylinder 30 (30') affects the direction and magnitude of helical force induced by a helical actuator. In the preferred embodiment, the angle ϕ between the principle strain axis and longitudinal axis of the hollow cylinder 30 (30∝) is greater than zero, preferably between 10 and 80 degrees.

Figure 1F:
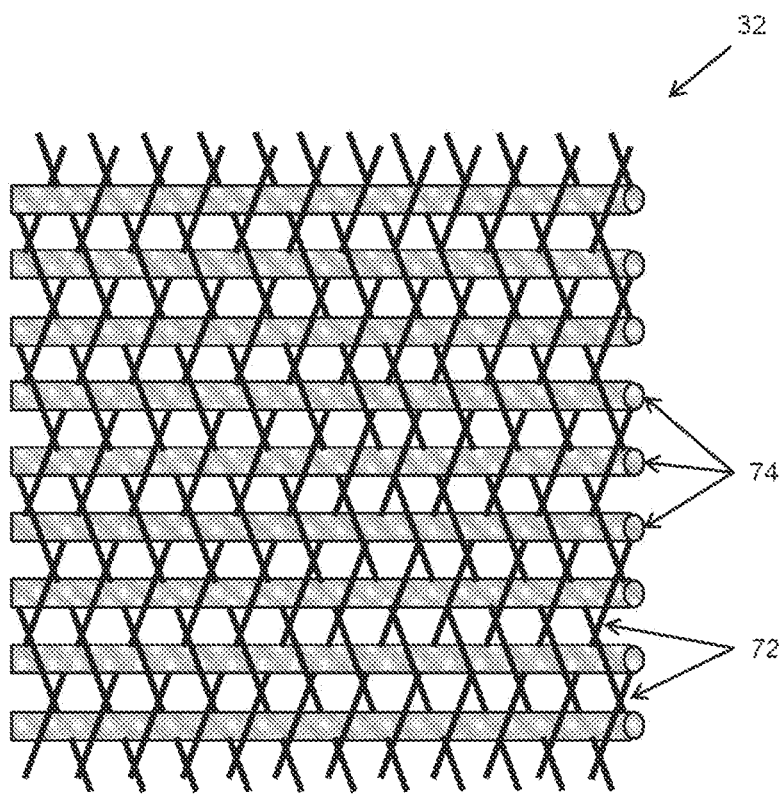
FIG. 1F is diagrammatic illustration of an anisotropic fabric for use in a helical actuator of a robotic forearm orthosis.

Referring to FIG. 1F, the anisotropic sheet material 32 consists essentially of a matrix 72 and a plurality of parallel elastomeric strands 74 embedded in the matrix. The matrix 72 may consist of natural or synthetic thread, yarn, or similar material knitted or woven into a mesh or repeating loops. In some embodiments, the matrix comprises a polyester weft knit, and the warp comprises the parallel elastomeric strands 74 embedded in a single direction in the weft knit. As stated, the plurality of elastomeric strands 74 are oriented in parallel to one another in a single direction, thereby producing an anisotropic response to force parallel to the strands and perpendicular to the strands. The principle strain axis of the anisotropic sheet material corresponds to the orientation of the parallel elastomeric strands. In the preferred embodiment, the principle strain axis of the anisotropic sheet material 32 is characterized by a spring constant, i.e., a stiffness value, of approximately 300 N/m for a sample having a width of 48 mm (perpendicular to the principle strain axis). Assuming that the stiffness increases proportionally with width, the material stiffness is approximately 6.25 N/m per mm width. Different applications may, however, employ stronger or weaker actuators, which may necessitate higher or lower stiffness values, i.e., stiffness values ranging between 3 and 12 N/m per mm width.

In the preferred embodiment, the parallel elastomeric strands 74 comprise a rubber material or synthetic rubber material marketed under various trademarks including Spandex, Lycra or Elastane. In the preferred embodiment, the anisotropic sheet material 32 comprises approximately six to seven elastomeric strands per centimeter, each strand having a diameter of approximately 0.60 to 0.75 mm. The matrix may include a natural or synthetic thread such as Nylon or Polyester, for example.

FIGS. 2A-2E illustrate a second embodiment of the robotic orthosis device. In this embodiment, the helical actuators are affixed to the dorsal and ventral sides of the forearm (instead of co-located on the ventral side as in FIG. 1A. Moreover, instead of using a whole sleeve to affix the actuators to the body, the second embodiment employs a user mounting system comprising rigid interfaces with hydrogel-based pads to hold the robotic orthosis device to the body. The user mounting system may further comprise bands with hook and loop type fasteners around the user's arm and interfaces to assist in hold the device to the body.

Figure 2A:
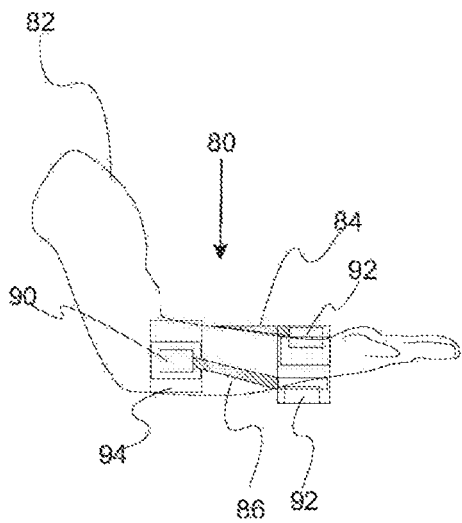
FIG. 2A-2B is a diagrammatic illustration of a robotic forearm orthosis in a supination mode and pronation mode.
Figure 2B:
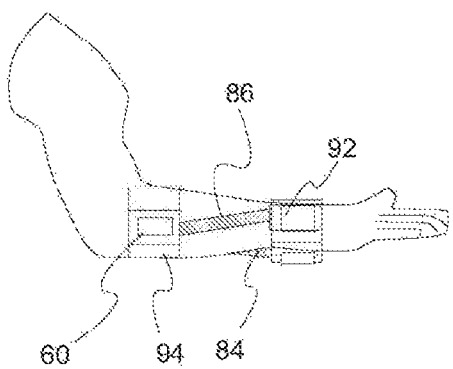

With reference to FIG. 2A, the robotic orthosis device 80 worn by a user 82 includes supination actuator 84 for supination and pronation actuator 86 for pronation. The supination actuator 84 and pronation actuator 86 are each helical actuators of the design set forth above with respect to the description of FIGS. 1A-1F. The ends of the supination actuator 84 and pronation actuator 86 are affixed to the user by means of a pair of rigid interfaces 90, 92 configured to conform and attach to a subject's forearm. When activated, each of the actuators 84, 86 generates a torque to rotate the user's wrist one direction or the other. That is, the actuators 84, 86 apply a force against the proximal end of the robotic orthosis device 80 to induce movement of the distal end of the robotic orthosis device.

In one embodiment, the rigid interfaces 90, 92 comprise a hydrogel (or other gel like interface) pad configured to adhere the rigid interfaces to user's body. The hydrogel pads may include various embedded sensors, including but not limited to electromyography, force and pressure sensors. A first rigid interface 90 can be attached at the proximal end of the forearm (or other joint) near the elbow and a second rigid interface 92 attached at the distal end of the forearm near the wrist (or distal end of other joint). An band 94, either elastic or inelastic, may also be wrapped around the interfaces, thereby helping to hold the robotic orthosis device 80 against the user's arm 82.

Figure 2C:
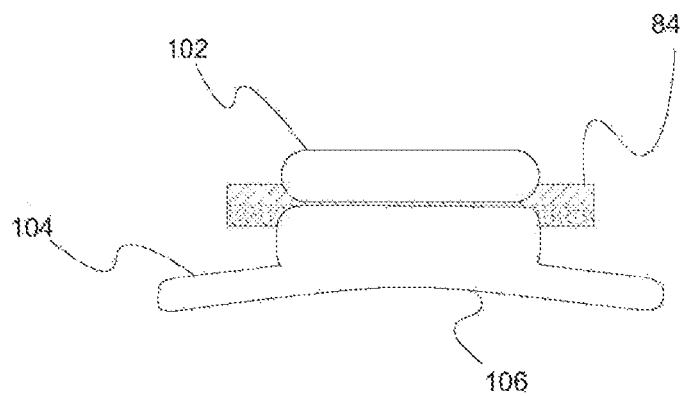
FIGS. 2C-2E are various views of a helical actuator for use in a robotic forearm orthosis.
Figure 2D:
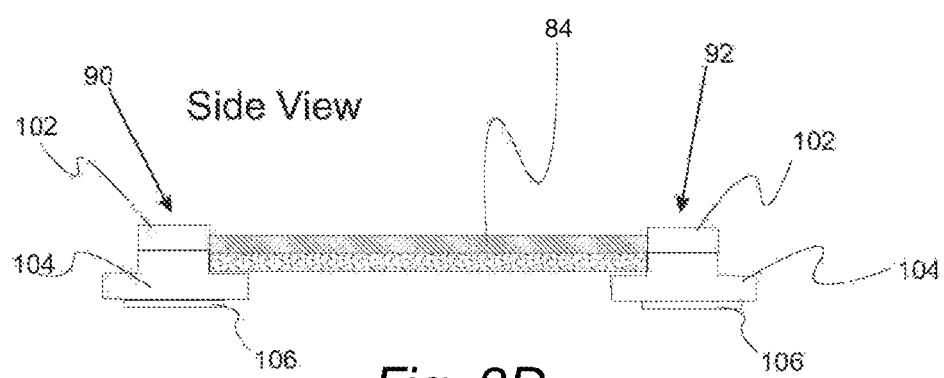
Figure 2E:
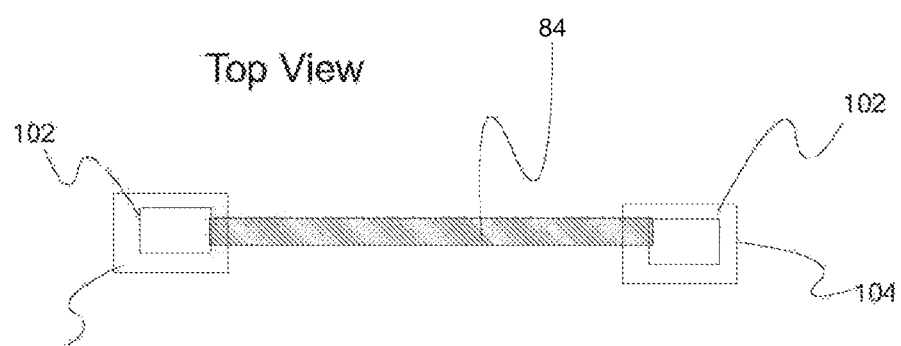

FIG. 2C is a front view illustration of a rigid interface. FIG. 2D-2E provides side and top views of a fabric-based helical actuator with rigid interfaces at either end of each actuator 84, 86. Each rigid interface 90, 92 includes a rigid top 102, rigid base 104, and pad 106 (or adhesive) attached directly to the base 104. The pad 106 (or adhesive) comprises hydrogel or similar adhesive and one or more embedded sensors and/or electrical stimulators. Types of electrical stimulators that may be embedded in the hydrogel pads may include, but are not limited to, Transcutaneous electrical nerve stimulation (TENS) Unit Pads which are electrotherapy pads for electrical stimulation of the muscle and/or sensory nerves (EMS) muscle. In some embodiments, the hydrogel pads include one or more sensors configured to (1) detect the user's muscle activation and/or force interaction, and (2) the detected signal used by the pressure controller to active the appropriate actuator. In another embodiment, the hydrogel pads include one or more electrical contacts or electrical stimulators configured to stimulate the user's muscles and/or sensory nerves in a way related to, or in conjunction with, the actuator's activations. If a user attempts to rotate his wrist a particular direction, the sensor detects the activation and causes the pressure controller to activate the actuator to augment the user's movement with the additional force of the actuator.

Fabric-Based Helical Actuators

Illustrated in FIGS. 3A-3C are a right arm and an exemplary robotic orthosis device in three different modes of operation, namely the supinate mode, neutral mode, and pronate mode. In the supinate mode, the supination actuator is activated to rotate the user's wrist outward with respect to the right elbow. As the wrist is rotated outward, the user's right thumb rotates clockwise with respect to the elbow. As shown, the user's wrist is rotated approximately 70 degrees with respect to the neutral position in which neither helical actuator is activated, i.e. the position in which the user's thumb is directed upward. A maximum angular displacement of approximately 70 degrees is achieved by pressurizing the supination actuator to a maximum pressure of approximately 100 psi. Angular rotation of less than 70 degrees is achieved using less than maximum pressure.

In the pronate mode, the pronation actuator is activated to rotate the user's wrist inward with respect to the right elbow. As the wrist is rotated inward, the user's right thumb rotates counter-clockwise with respect to the elbow. As shown, the user's wrist is rotated approximately 70 degrees with respect to the neutral position. The maximum angular displacement of 70 degrees is achieved by fully pressurizing the pronation actuator to about 100 psi. Angular rotation of less than 70 degrees is achieved using less than maximum pressure.

Figure 4A:
FIGS. 4A-4B are diagrammatic illustrations of a fabric-based bending actuator comprising first material configured to strain longitudinally and a second material that is inextensible.
Figure 4B:
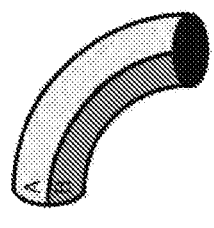

The supination actuator and pronation actuator are fabric-based helical actuators in the preferred embodiment. In a fabric-based helical actuator, helical displacement of the actuator is achieved through the deformation of compliant regions of the actuator structure in response to air pressure. Illustrated in FIGS. 4A-4B is a conceptual model of a two-component actuator to demonstrate the principle of operation of a fabric-based helical actuator. Consider a hollow cylinder composed of two thin fabric materials and sealed ends. If both materials are isotropically inextensible, then inflating the cylinder causes it to become more rigid. However, if one material, i.e., material-A, can strain along the longitudinal axis while remaining inextensible in the orthogonal (radial) direction, then pressurizing the cylinder causes material-A to lengthen longitudinally, while the length of the strain-limiting material, i.e., material-B, remains fixed. This lengthening of material-A causes the upper side of the hollow cylinder to bend downward toward material-B. Let $\phi$ denote the angle between the principle strain axis of the anisotropic material and the longitudinal axis of the actuator. If $\phi=0$ degrees, then when inflated, bending will be achieved, as outlined above. If $\phi=90$ degrees, then inflation will cause radial expansion of the anisotropic layer, resulting in rigidization with no longitudinal length change. However, if the angle $\phi \in$ (0 degrees, 90 degrees), helical motions are realized.

Fabrication

Stage one of the fabrication process is illustrated in 5A. The anisotropic sheet material (also referred to as the "knit layer") is a knit elastic band sold under the name "Cisone" and identified as "6 Inches Wide White Heavy Stretch High Elasticity Knit Elastic Band". The strain-limiting fabric is a ballistic nylon available from "Magna Fabrics" of Cresskill, N.J. and identified as "1050 Denier Coated Ballistic Nylon Fabric". Prior to pattern cutting, the knit elastic strands must be aligned with the chosen knit angle $\phi$. The knit angle $\phi$ is the angle between the longitudinal axis of the actuator and the principle strain axis of the anisotropic sheet material. The actuator sleeve, which is composed of the two fabrics, is constructed by cutting rectangular patterns (in our case length $L_p$=19 cm, width $\omega p$=4 cm) from their respective materials. Next, the rectangular patterns are sewn together at the two longitudinal edges using a zig-zag stitch to prevent unravelling of the fabric edges. Subsequently, two straight stitches, with width $\omega_a$=2.5 cm between, are sewn down the center of the sleeve, forming the pocket for the bladder. The width $\omega_a$ is chosen to allow the bladder assembly to be pulled through the sleeve.

Figure 5A:
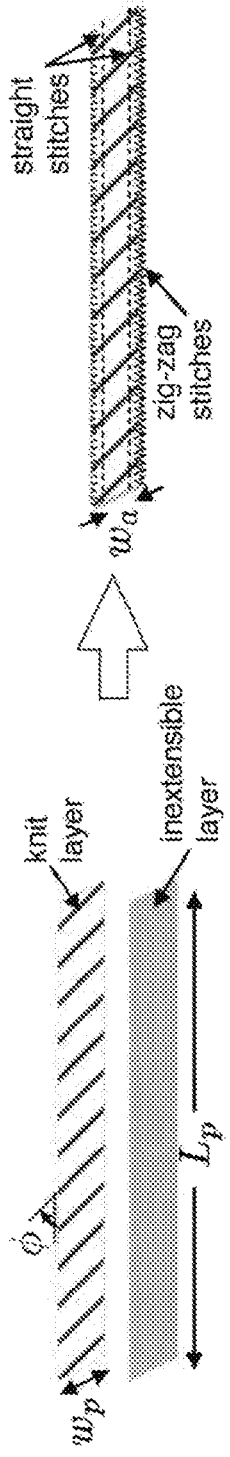
FIGS. 5A-5C are diagrammatic illustrations of a fabrication procedure for a robotic forearm orthosis.
Figure 5B:
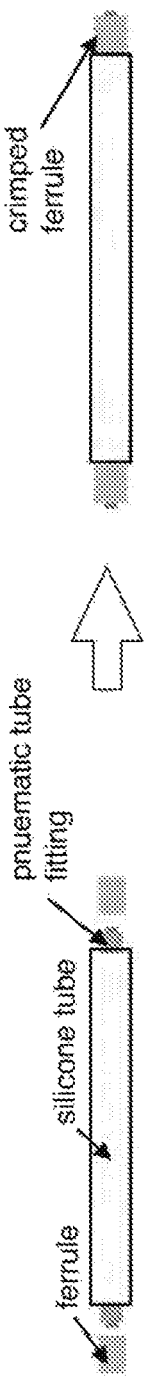

In the next fabrication stage, the bladder is assembled, as shown in FIG. 5B. Two push-to-connect tube fittings (called "Push-to-Connect Tube Fitting for Air/Water", "Straight Adapter", and "5/32 inch Tube OD×1/8 NPT Male" are available from McMaster-Carr of Los Angeles, Calif.) are inserted in both ends of a silicon tube ("Silicone Rubber Tubing, Durometer 35A, 1/4 inch ID, 3/8 inch OD" from McMaster-Carr) with length $L_p$. Next, two brass hose ferrules ("0.700 inch Brass Hose Ferrule" from Grainger of Los Angeles, Calif.), are positioned around the silicon tube and push-to-connect tube fittings and crimped to seal the bladder. The push-to-connect tube fittings are easily interfaced with pneumatic tubing ("High-Pressure Nylon Tubing, 0.106 inch ID. 5/32 inch OD" from McMaster-Carr), e.g., one one end and a plug on the other ("Push-to-Connect Tube Fitting for Air, Plug, 5/32 inch Stem OD" from McMaster-Carr).

Figure 5C:
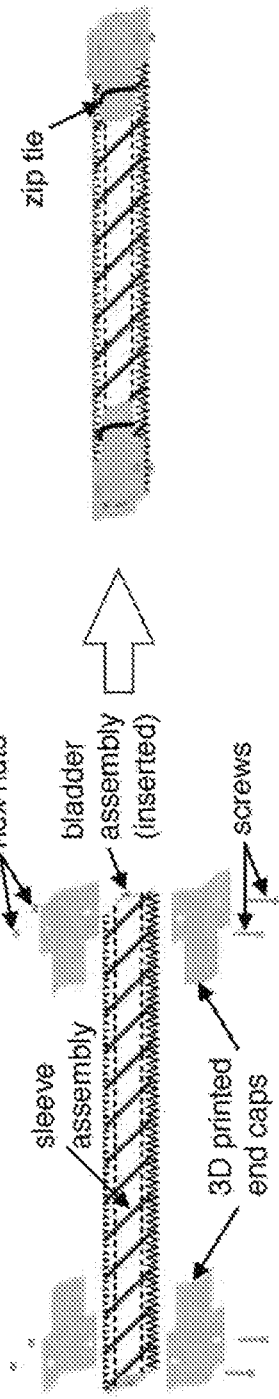

As illustrated in FIG. 5C, the last stage of fabrication combines the two subassemblies by securing the bladder to the sleeve using custom 3D printed end caps. First, the bladder is inserted into the actuator sleeve. The end caps are designed to encapsulate the sleeve and cylindrical hose ferrules at the ends of the bladder, thereby preventing the bladder from escaping the sleeve. The end caps are secured together using screws hex nuts. Note that, before the end caps are installed, holes are punch through the sleeve. The holes allow the screws through the sleeve, and accommodate a zip-tie, installed last, providing increased support at the distal ends of the end caps.

Pressure Control

Figure 6:
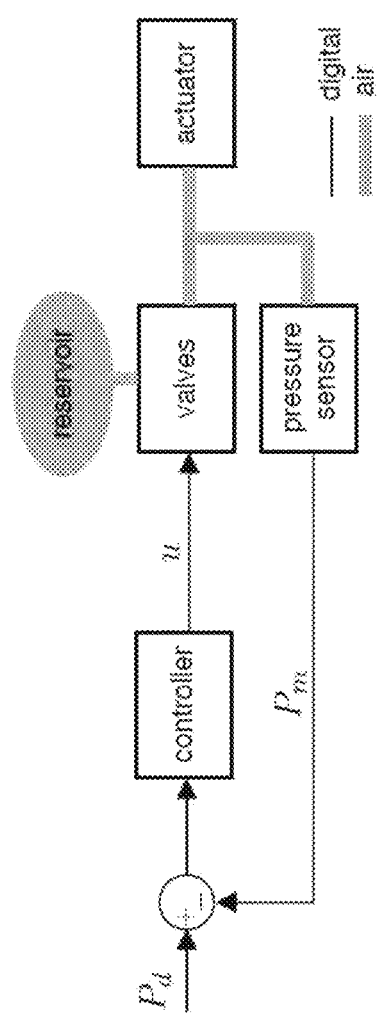
FIG. 6 is a schematic illustration of a single actuator control architecture configured to maintain the actuator's internal pressure $P_m$ at the desired pressure $P_d$.

The internal pressure $P_m$ of a single fabric-based helical actuator is maintained at a desired pressure $P_d$ using on-off control of two solenoid valves (SMC, SY113-SMO-PM-F), one valve connected to an air compressor or air reservoir (maintained at 860 kPa (125 psi)), and the other an exhaust valve. A functional block diagram illustrating the controller architecture is depicted in FIG. 6. The internal pressure of the actuator is measured with a piezoresistive silicon pressure sensor (model number "HSC-SANN150PG2A3" from Honeywell of Charlotte, N.C.), connected to the actuator with pneumatic tubing. The controller determines the state u of the valves as follows:

$$u = \begin{cases} 1 & \text{if } P_d - P_m > 0 \\ 0 & \text{if } -\bar{e} \le P_d - P_m \le 0 \\ -1 & \text{if } P_d - P_m < -\bar{e} \end{cases} \quad (1)$$

where the interval $[-\bar{e}, 0]$ is the deadband, and u=1 the solenoid valve connected to the air compressor or air reservoir is on (i.e., open), u=1 the exhaust solenoid valve is on, and when u=0 both valves are off (i.e., remain closed). The deadband, reduces high frequency valve switching and is selected as $\bar{e}$=14 kPa (2 psi). The control loop, implemented on a BeagleBone Black (REV C.) development platform with custom software, has a loop frequency of 1 kHz.

Experimental Evaluations

Figure 7:
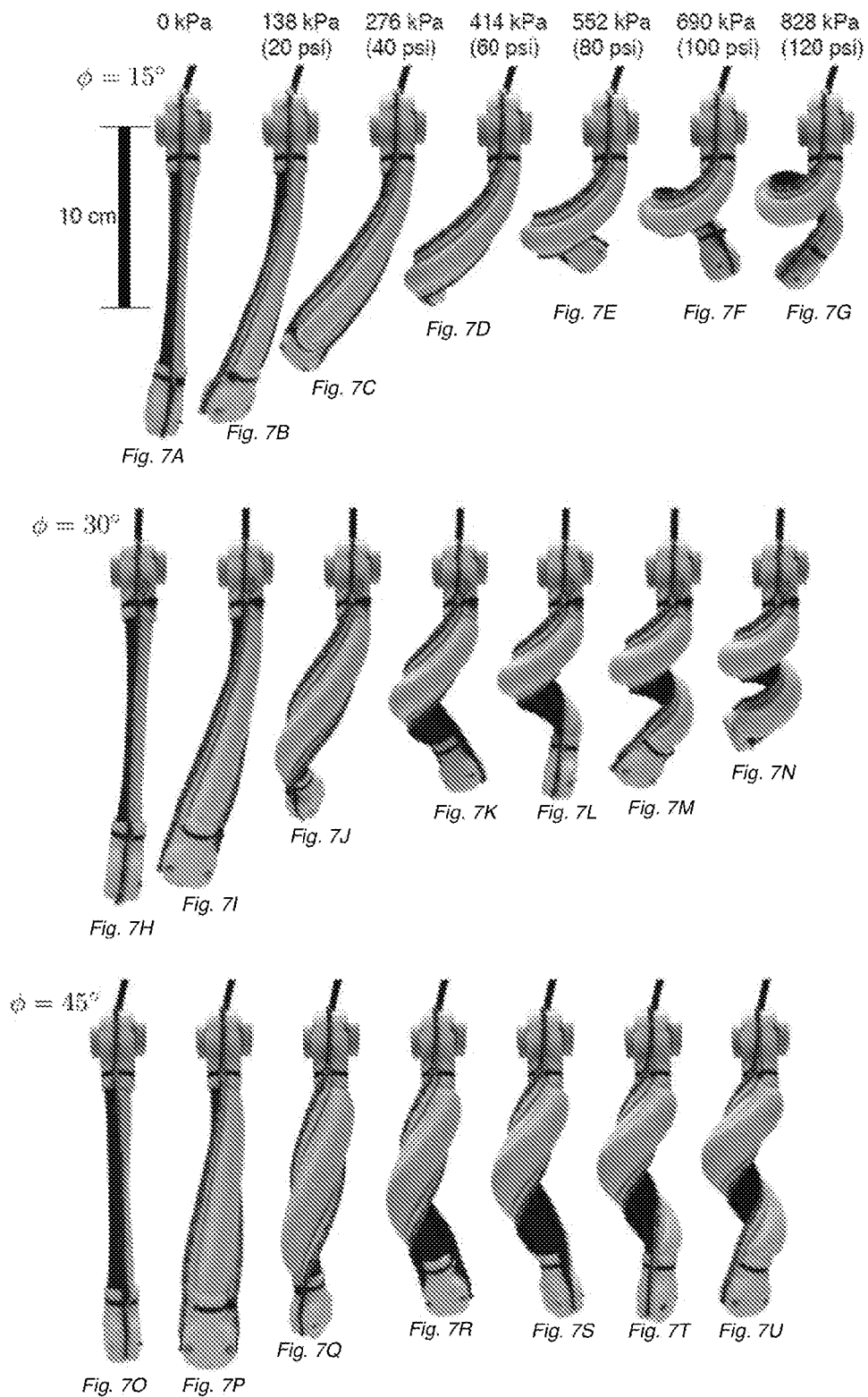
FIGS. 7A-7U illustrate a series of fabric-based actuators, where the knit angles along the vertical axis and the inflation pressure varies along the horizontal axis.

To investigate the effect of knit angle φ on the actuator mechanics, three actuators were constructed with different knit angles, namely φ=15 degrees in the uppermost row, φ=30 degrees in the middle row, and φ=45 degrees in the lowermost row. While fixed at one end, each actuator was pressurized from 0 kPa to 828 KPa (120 psi) in increments of 138 kPa (20 psi). The sequence of pressurized states for each actuator is shown in FIGS. 7A-7U where pressure is successively increased from left to right. As the knit angle φ is increased, the winding radius decreased and pitch length (distance between successive windings) increased. Note that positive values of φ correspond to right-handed helices.

Figure 8:
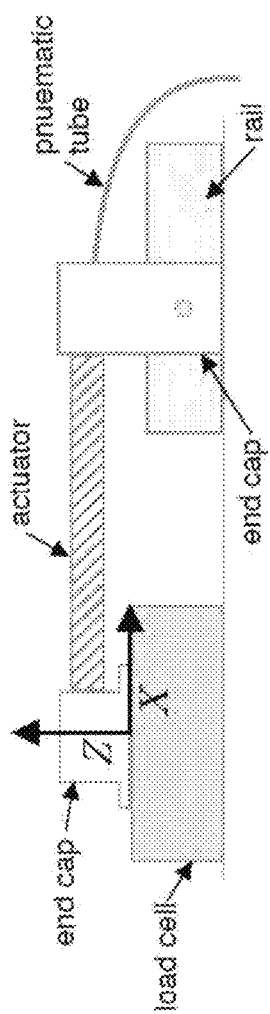
FIG. 8 is a schematic representation of an experimental setup for measuring torque produced by a fabric-based helical actuator.
Figure 9:
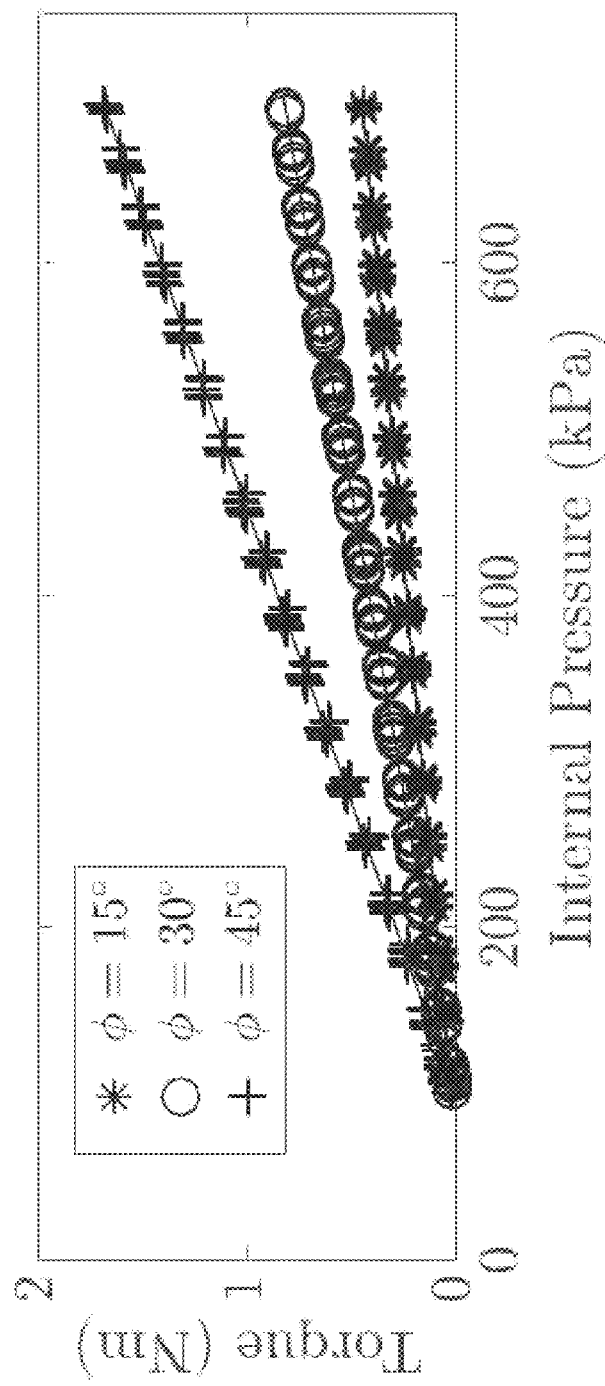
FIG. 9 is a scatter plot of torque versus pressure data, for each knit angle ϕ, during isometric experiments.

The torque characteristic of the three fabric-based helical actuators, i.e., with knit angle φ=15, 30, and 45 degrees, was empirically evaluated by isometrically constraining the actuator, gradually pressurizing/depressurizing (i.e., as a staircase function), and measuring the magnitude of generated torque with a multi-axis force/torque sensor. The experimental setup is illustrated in FIG. 8. The results indicate that as knit angle φ increased, the magnitude of achieved torque (measured along X-axis) increased. This can be seen in FIG. 9, which shows the magnitude of torque versus internal pressure for each actuator. The results indicate a negligible amount of hysteresis between inflating/deflating, and that torque is well approximated by a linear dependence on pressure. The maximum torques, at an inflation pressure of 700 kPa (100 psi), were approximately 0.45 Nm, 0.82 Nm, and 1.7 Nm, for knit angles 15, 30, and 45 degrees, respectively.

Figure 10:
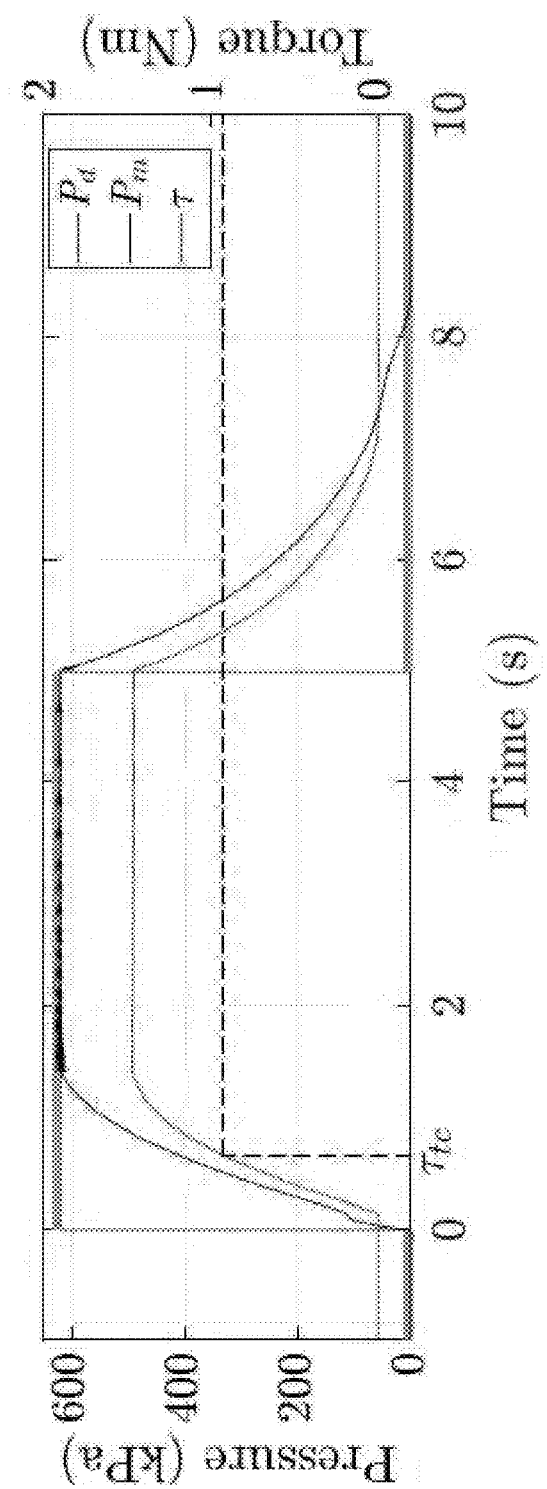
FIG. 10 is a graph illustrating a step response for a single actuator.

The controller performance was characterized with a step response using the setup described above in context of FIG. 8 and the actuator with knit angle φ=45 degrees. The internal pressure $P_m$ and actuator torque z were measured simultaneously, while the desired pressure $P_d$ was set to 620 kPa (90 psi) for 5 seconds. The pressure $P_m$ and torque z responses is illustrated in FIG. 10. The torque time constant was estimated to be $\tau_{ts}$=0.67, (i.e., the time to reach 63% of steady state), corresponding to an approximate bandwidth of 0.24 Hz.

Robotic Orthosis Design and Fabrication

Practical consideration for the design of the robotic orthosis include comfortability, sufficient torque assistance, and ease of donning/doffing. The challenges are to physically attach the device to the user, and adequately transmit the assistive torques.

Referring to FIG. 11A, the preferred embodiment of the robotic orthosis device employs one or more sleeves incorporating an antagonistic pair of fabric-based helical actuators secured using rigid support structures. The robotic orthosis device 1100 includes the wearable neoprene sleeve 1110, a pocket 1120 for a first rigid support (see FIG. 11C) adjacent to wrist, a pocket 1130 for a second rigid support (see FIG. 11D) adjacent to the elbow, a palm strap 1140, a hole configured to receive the user's thumb 1124, a wrist strap 1150, and a forearm strap 1160. Each of the straps 1140, 1150, 1160 includes a fastener, e.g. a fabric hook material 1170 and fabric loop material 1172 configured to detachably attach the strap to the user. A first set of holes 1122 is configured to mount a wrist/palm support structure recessed in the pocket 1120, while the second set of holes 1132 is configured to mount a forearm support structure recessed in the pocket 1130.

Figure 11B:
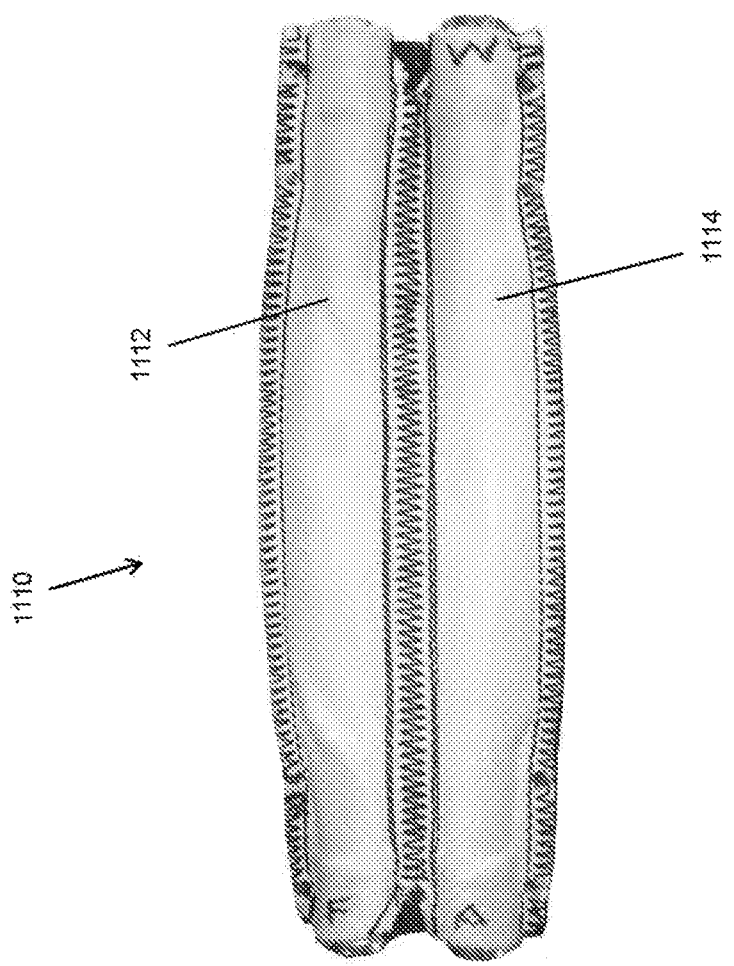
FIG. 11B is a top view of the fabric portion of a pair of antagonist fabric-based helical actuators.
Figures 11C, 11D:
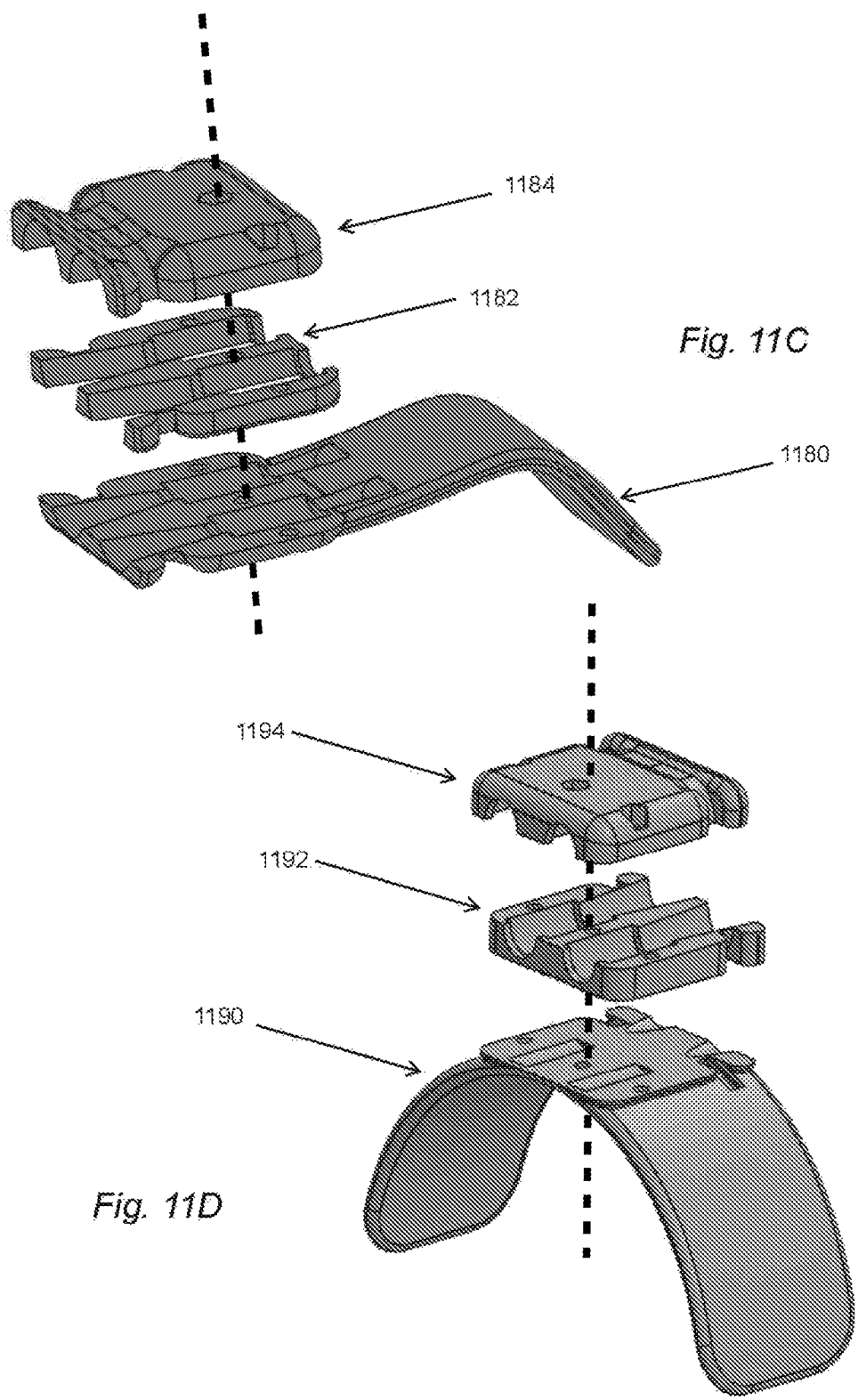
FIG. 11C is an exploded view of wrist support structure.
FIG. 11D is an exploded view of the forearm support structure.

The fabric portion 1110 of the pair of helical actuators 1112, 1114 is illustrated in FIG. 11B. The rigid support coinciding with the user's wrist is illustrated in FIG. 11C, and the rigid support configured to attach below the user's elbow is illustrated in FIG. 11D. The palmar side of the sleeve is constructed from neoprene or flexible water-resistant material, and features a thumb hole, pockets for the rigid inserts, hole patterns for securing the rigid inserts and actuators, and three elastic straps comprising hook and loop fasteners or other type of clasp. The dorsal side of the sleeve is a flexible synthetic material such as Lycra or Spandex.

The robotic orthosis device in the preferred embodiment comprises two antagonistic helical actuators, one with a knit angle φ=45 degrees (producing a right helix when inflated) and the other with a knit angle φ=−45 degrees (producing a left helix when inflated). Each actuator can produce up to 1.7 Nm of torque. The knit angle of each helical actuator is measured with respect to the longitudinal axis of the unpressurized helical actuator and the robotic orthosis device more generally. The longitudinal axis of the supination actuator and longitudinal axis of the pronation actuator are substantially parallel to one another.

Referring to FIGS. 11A-11D, the robotic orthosis device comprises support structures serving two functions: (1) attaching the actuators to the sleeve, and (2) transmitting the generated torques. The wrist support structure shown in FIG. 11C consists of a supporting insert 1180 (ergonomically shaped to fit the wrist and palm), a spacer 1182, and cap 1184. The design is a modified version of the 3D printed end caps, but incorporates a wrist/palm support structure. During assembly, the wrist insert 1180 is placed inside the wrist pocket 1120 of the sleeve. The spacer 1182 provides a cylindrical region for the fabric-based actuators. Next, the cap 1184 is placed on top and screws/nuts used to secure the assembly via the first set of holes 1122. The forearm support structure, ergonomically shaped for the forearm, is identically assembled. The forearm support structure in FIG. 11D consists of a supporting insert 1190 ergonomically shaped to fit the upper forearm, a spacer 1192, and cap 114. During assembly, the forearm insert 1190 is placed inside the wrist pocket 1130 of the sleeve. The spacer 1192 provides a cylindrical region for the fabric-based actuators. Next, the cap 1194 is placed on top and screws/nuts used to secure the assembly to the robotic orthosis device 1100 via the second set of holes 1132.

To don the device, the user inserts their hand through the sleeve, then fastens the elastic hook and loop straps, which are situated such that the straps secure the rigid wrist and forearm supports, as shown in FIGS. 3A-3C. The total weight of the device is approximately 200 grams, not including the pressure control system, valves, sensors, or reservoir tank.

One or more embodiments of the present invention may be implemented with one or more computer readable media, wherein each medium may be configured to include thereon data or computer executable instructions for manipulating data. The computer executable instructions include data structures, objects, programs, routines, or other program modules that may be accessed by a processing system, such as one associated with a general-purpose computer or processor capable of performing various different functions or one associated with a special-purpose computer capable of performing a limited number of functions. Computer executable instructions cause the processing system to perform a particular function or group of functions and are examples of program code means for implementing steps for methods disclosed herein. Furthermore, a particular sequence of the executable instructions provides an example of corresponding acts that may be used to implement such steps. Examples of computer readable media include random-access memory ("RAM"), read-only memory ("ROM"), programmable read-only memory ("PROM"), erasable programmable read-only memory ("EPROM"), electrically erasable programmable read-only memory ("EEPROM"), compact disk read-only memory ("CD-ROM"), or any other device or component that is capable of providing data or executable instructions that may be accessed by a processing system. Examples of mass storage devices incorporating computer readable media include hard disk drives, magnetic disk drives, tape drives, optical disk drives, and solid state memory chips, for example. The term processor as used herein refers to a number of processing devices including personal computing devices, servers, general purpose computers, special purpose computers, application-specific integrated circuit (ASIC), and digital/analog circuits with discrete components, for example.

To the extent materials to fabricate the objects described herein are connected to a particular source, comparable materials may be available from other sources, and the disclosures herein of the sources of materials is for representative purposes only, and not intended to be limiting; provided, that the materials sourced from other suppliers possess the same properties noted above.

Although the description above contains many specifications, these should not be construed as limiting the scope of the invention but as merely providing illustrations of some of the presently preferred embodiments of this invention.

Therefore, the invention has been disclosed by way of example and not limitation, and reference should be made to the following claims to determine the scope of the present invention.

What is claimed is:

1. A robotic orthosis device, comprising:
a user mounting system configured to attach to a user's forearm;
at least one helical actuator comprising:
a cylinder having a longitudinal axis, the cylinder comprising:
an anisotropic sheet material comprising a matrix and elastomeric strands embedded within the matrix to define a principle strain axis, wherein all the elastomeric strands are oriented in a first direction and the first direction is different than the longitudinal axis, wherein the principle strain axis is characterized by a spring constant ranging from 3 N/m per mm width to 12 N/m per mm width;
a base sheet material affixed to the anisotropic sheet material, wherein the base sheet material is strain-limiting along the longitudinal axis;
wherein the anisotropic sheet material is more extendible in a direction along the longitudinal axis than the base sheet material; and
a bladder disposed within the cylinder, wherein the bladder is configured to inflate and apply pressure against the cylinder.

2. The robotic orthosis device of claim 1, wherein the at least one helical actuator comprises a supination actuator and a pronation actuator.

3. The robotic orthosis device of claim 2, wherein the supination actuator comprises a first anisotropic sheet material and the pronation actuator comprises a second anisotropic sheet material.

4. The robotic orthosis device of claim 3, wherein the first anisotropic sheet material and second anisotropic sheet material are affixed to a single base sheet material.

5. The robotic orthosis device of claim 4, wherein the first anisotropic sheet material is characterized by a first principle strain axis, and the second anisotropic sheet material is characterized by a second principle strain axis.

6. The robotic orthosis device of claim 5, wherein a first knit angle between the first principle strain axis and the longitudinal axis is between 10 and 80 degrees, and a second knit angle between the first principle strain axis and the longitudinal axis is between −10 and −80 degrees.

7. The robotic orthosis device of claim 3, wherein the user mounting system comprises a flexible sleeve.

8. The robotic orthosis device of claim 3, wherein the user mounting system comprises at least one rigid interface.

9. The robotic orthosis device of claim 8, further comprising a hydrogel pad operatively connected to the at least one rigid interface.

10. The robotic orthosis device of claim 9, wherein the hydrogel pad comprises one or more embedded sensors or electric contacts configured to provide electrical stimulation.

11. The robotic orthosis device of claim 10, wherein the hydrogel pad comprises one or more pressure sensors configured to sense muscle activation of the user.

12. The robotic orthosis device of claim 11, further comprising a pressure control system operatively coupled to the one or more pressure sensors, wherein the pressure control system is configured to drive the supination actuator and the pronation actuator based, in part, on signals from the one or more pressure sensors.

13. The robotic orthosis device of claim 3, wherein the bladder is configured to receive a working fluid, and the working fluid comprises air.

14. A robotic orthosis, comprising:
a user mounting system configured to attach to a user's forearm;
a first helical actuator comprising:
a first cylinder having a first longitudinal axis, the first cylinder comprising:
a first anisotropic sheet material comprising elastomeric strands, wherein all the elastomeric strands are oriented in a first direction and the first direction is different than the first longitudinal axis;
a base sheet material affixed to the first anisotropic sheet material, wherein the base sheet material is strain-limiting along the longitudinal axis;
wherein the first anisotropic sheet material is more extendible in a first extension direction along the longitudinal axis than the base sheet material; and
a first bladder disposed within the first cylinder, the first bladder comprising: an inlet configured to receive a working fluid; and an outlet configured to expel working fluid;

wherein the first bladder is configured to inflate and apply pressure against the first cylinder and rotate the first cylinder in a first rotation direction about the first longitudinal axis; and a second helical actuator, comprising:
  a second cylinder having a second longitudinal axis, the second cylinder comprising a second anisotropic sheet material comprising elastomeric strands, wherein all the elastomeric strands of the second anisotropic sheet are oriented in a second direction and the second direction is different than the second longitudinal axis, wherein the second anisotropic sheet material is affixed to a second base sheet material;
  wherein the second anisotropic sheet material is more extendible in a second extension direction along the second longitudinal axis than the second base sheet material; and
  a second bladder disposed within the second cylinder;
  wherein the second bladder is configured to inflate and apply pressure against the second cylinder and rotate the second cylinder about the second longitudinal axis in a second rotation direction opposite the first rotation direction relative to the first cylinder.

15. A fabric-based helical actuator, comprising:

a first cylinder having a longitudinal axis, the first cylinder comprising:
  a first anisotropic sheet material comprising a matrix and a first set of elastomeric strands, wherein the first set of elastomeric strands are embedded in the matrix and all the elastomeric strands are oriented in a first direction and the first direction is different than the longitudinal axis; and
  a base sheet material affixed to the first anisotropic sheet material, wherein the base sheet material is strain-limiting along the longitudinal axis, whereby the first anisotropic sheet material is more extendible in a first extension direction along the longitudinal axis than the base sheet material;
  a first bladder disposed within the first cylinder, wherein the first bladder is configured to inflate and apply pressure against the first cylinder, wherein pressure against the first cylinder by the first bladder causes the first cylinder to rotate in a first rotation direction;

a second cylinder comprising a second anisotropic sheet material affixed to a second base sheet material, the second anisotropic sheet material comprising a second set of elastomeric strands; and a second bladder disposed within the second cylinder, wherein the second bladder is configured to inflate and apply pressure against the second cylinder, wherein pressure against the second cylinder by the second bladder causes the second cylinder to rotate in a second rotation direction.

16. The robotic orthosis device of claim 1, wherein the user mounting system comprises a wrist insert and a forearm insert, wherein the wrist insert comprises a wrist support structure and a palm support structure, wherein the wrist support structure and the palm support structure are ergonomically shaped to fit a wrist and a palm of the user, and wherein the forearm insert is ergonomically shaped to fit an upper forearm of the user.

17. The robotic orthosis device of claim 16, wherein the user mounting system further comprises:
  a first spacer operatively connectable to the wrist insert;
  a first cap operatively connectable to the first spacer;
  a second spacer operatively connectable to the forearm insert; and
  a second cap operatively connectable to the second spacer, wherein the first spacer and the first cap are configured to attach a first end of the at least one helical actuator to the wrist insert, and the second spacer and the second cap are configured to attach a second end of the at least one helical actuator to the forearm insert.

18. The robotic orthosis device of claim 17, wherein the user mounting system further comprises a sleeve for donning on the forearm of the user, the sleeve comprising:
  a first pocket configured for receiving the wrist insert;
  a second pocket configured for receiving the forearm insert;
  a thumb hole adjacent to the first pocket through which a thumb of the user can be inserted;
  a palm strap to secure the sleeve to the palm;
  a wrist strap to secure the sleeve to the wrist; and
  a forearm strap to secure the sleeve to the forearm.

* * * * *